United States Patent [19]

Linsley et al.

[11] Patent Number: 4,803,169

[45] Date of Patent: Feb. 7, 1989

[54] ASSAY FOR HUMAN BREAST CANCER

[75] Inventors: Peter S. Linsley; Vincent W. Ochs; Diane Horn; Joseph P. Brown, all of Seattle, Wash.; David B. Ring, Redwood City, Calif.; Arthur E. Frankel, Chapel Hill, N.C.

[73] Assignee: Cetus Corporation, Emeryville, Calif.

[21] Appl. No.: 826,477

[22] Filed: Feb. 5, 1986

[51] Int. Cl.$^4$ ........................................... G01N 33/577
[52] U.S. Cl. .......................................... 435/7; 424/85.8; 436/501; 436/518; 436/536; 436/548; 436/813; 530/387
[58] Field of Search ..................... 435/7; 436/518, 501, 436/536, 548, 813; 530/387; 424/85

[56] References Cited

U.S. PATENT DOCUMENTS 4,522,918  6/1985  Schlom et al. .......................... 435/68
4,753,894  6/1988  Frankel et al. ....................... 436/548

OTHER PUBLICATIONS

Frankel et al "Tissue Distribution of Breast Cancer-Associated Antigens Defined by Monoclonal Antibodies", J. Biol. Res. Mod. 4:273–286 1985.
Ceriani et al, *PNAS* (1982) 79:5420–5424.
Burchell, J. et al, *Int J Cancer* (1984) 34:763–768.
Hayes, D. F., *J Clin Invest* (1985) 75:1671–1678.
Roberto L. Ceriani et al. (1983) Somatic Cell Genetics, 9:415–427.

*Primary Examiner*—Christine M. Nucker
*Attorney, Agent, or Firm*—Ciotti & Murashige, Irell & Manella

[57] ABSTRACT

Methods are disclosed for detecting, staging and monitoring breast cancer. The methods involve determining the amount of certain antigens, designated W1 and W9, in serum via quantitative immunoassays using anti-W1 or anti-W9 monoclonal antibodies. The amount detected is compared with amounts of the antigen found in normal sera, sera from breast cancer patients of predetermined stage, or other samples of the patient's own serum, depending upon the purpose of the assay.

11 Claims, 2 Drawing Sheets

ASSAY FOR HUMAN BREAST CANCER

TECHNICAL FIELD

This invention is in the field of cancer diagnosis and monitoring. More particularly it relates to a method for diagnosing breast cancer or monitoring the status of breast cancer in breast cancer patients by determining the amount of certain antigens in body fluids such as serum by a quantitative immunoassay.

BACKGROUND ART

The progression of malignant diseases can in some cases be monitored by measuring serum levels of appropriate tumor markers. Numerous immunological assays for the detection of blood-borne tumor antigens have been developed, and of these, the most useful can be categorized into two broad groups. One group is based on actively secreted protein or glycoprotein antigens, such as alpha-fetoprotein and prostate specific antigen, and the second, on heavily glycosylated, high molecular weight antigens, such as carcinoembryonic antigen or the mucin-like antigens which are released by unknown mechanisms from a variety of tumor types.

Some varieties of cancers such as cancers of the breast—which are one of the largest classes of malignant disease in women—are not readily monitored using existing serological tests. Several potential serum markers for breast cancer are described in the literature. Ceriani et al, *PNAS* (1982) 79:5420-5424 describe mammary epithelial antigens which apparently are elevated in serum of patients with disseminated breast cancer. Burchell, J., et al, *Int J Cancer* (1984) 34: 763-768 have described monoclonal antibodies which detect high molecular weight mucin-like antigens elevated in patient serum. Hayes, D. F., *J Clin Invest* (1985) 75: 1671-1678 also describes a monoclonal antibody that recognizes a high molecular weight mammary epithelial antigen present in elevated amounts in the plasma of breast cancer patients. See also Papsidero, L. D., et al, *Cancer Res* (1984) 44: 4653-4657; TaylorPapadimitriou, J., et al, *Int J Cancer* (1981) 28: 17-28, and U.S. Pat. No. 4,522,918. In the absence of structural data for epitopes recognized by these antibodies it is impossible to determine the relationship between them or the antibodies used in the present invention. In any event, none of the previously described antibodies has been used as a basis for a widely accepted clinical assay.

Copending U.S. patent application Ser. No. 690,750 filed 11 Jan. 1985, now U.S. Pat. No. 4,753,894, describes a series of anti-breast cancer monoclonal antibodies. Those antibodies were identified based on their ability to bind selectively to human breast cancer cells and their efficacy as immunotoxins for breast cancer when conjugated to ricin A chain. The monoclonal antibodies that are used in the present invention methods are included in that series. The application states that the antibodies may be used in immunoassays to detect or monitor breast cancer. The specific assays it mentions are cellular rather than serological. The application does not suggest that any of the antigens recognized by the antibodies might be blood-borne breast cancer markers. The present invention is based on the finding that two of the antibodies described in that application recognize the same antigen or associated antigens which is/are elevated in breast cancer patient sera.

DISCLOSURE OF THE INVENTION

One aspect of the invention is a method of detecting breast cancer in a human patient comprising:

(a) determining the amount of an antigen selected from the group consisting of W1 antigen and W9 antigen in the body fluid of said patient by a quantitative immunoassay using a monoclonal antibody to said antigen; and (b) comparing the amount determined in (a) with the standard amount of said antigen that is present in corresponding body fluid of normal human subjects to determine whether the amount determined in (a) is substantially elevated relative to the amount present in the corresponding body fluid of normal human subjects, substantial elevation being an indication of breast cancer.

Another aspect of the invention is a method of monitoring the status of breast cancer in a human patient comprising:

(a) obtaining samples of a body fluid from the patient periodically over a given time interval;

(b) determining the amounts of an antigen selected from the group consisting of W1 antigen and W9 antigen in the samples by a quantitative immunoassay using a monoclonal antibody to said antigen; and (c) comparing the amounts, with an increase in amount being an indication of increased tumor burden and a decrease in amount being an indication of decreased tumor burden.

Another aspect of the invention is a method of determining the clinical stage of breast cancer in a human patient comprising:

(a) determining the amount of an antigen selected from the group consisting of W1 antigen and W9 antigen in a body fluid of said patient by a quantitative immunoassay using a monoclonal antibody to said antigen; and (b) comparing the amount determined in step (a) with predetermined amounts of said antigen that occur in corresponding body fluid of human breast cancer patients at the several stages of the disease.

MODES FOR CARRYING OUT THE INVENTION

Figure 1:
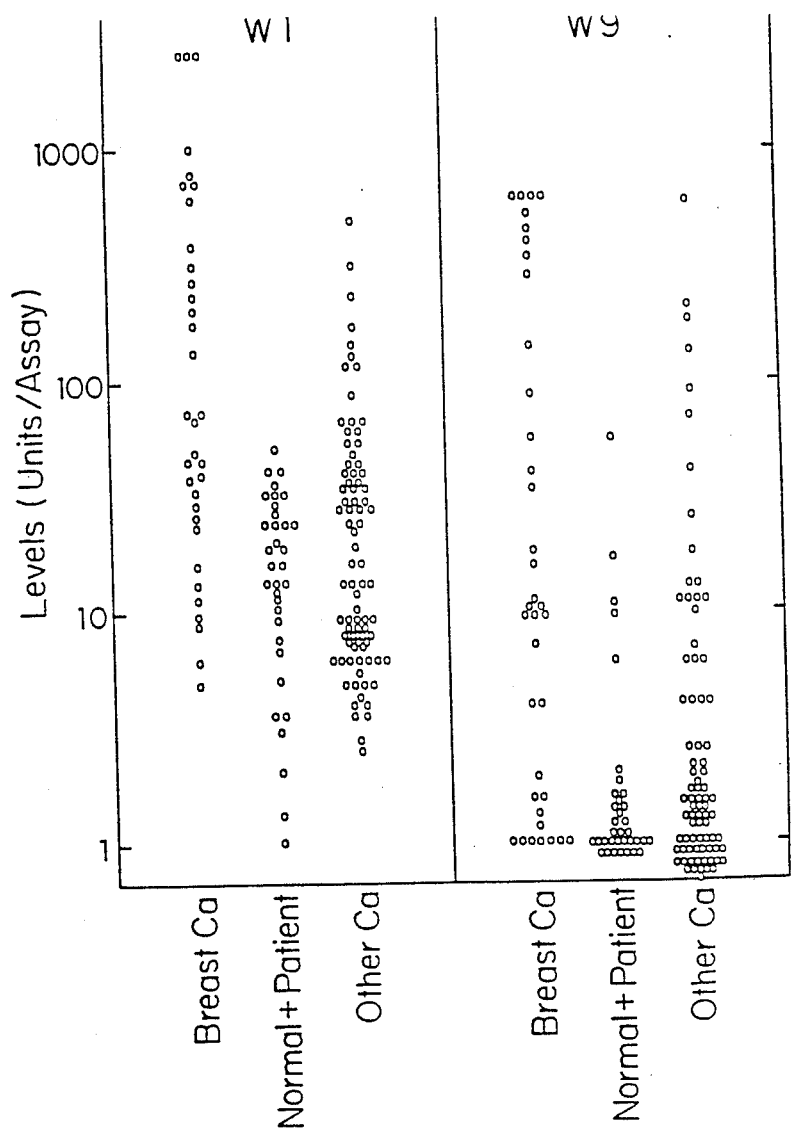
FIGS. 1 and 2 are graphs of the results of the assays described in the examples, infra.

As used herein the term "monoclonal antibody" means an antibody composition having a homogeneous antibody population. It is not intended to be limited as regards the species or source of the antibody or the manner in which it is made. The term is intended to include antigen binding fragments (e.g., Fab, F(ab')$_2$, Fv) as well as whole immunoglobulin.

As used herein with respect to the exemplified murine monoclonal anti-human breast cancer antibodies, the term "functional equivalent" means a monoclonal antibody that binds to the same epitope as the exemplified antibody as determined by binding inhibition studies.

As used herein to describe a human subject or subjects the term "normal" means that the subject or subjects have no detectable cancer.

The body fluid used in the assay will typically be serum. Other blood fractions (e.g., plasma) or body fluids such as breast fluid, effusion fluids (e.g., urine, or sputum) may be useful for detecting metastatic disease.

While in theory monoclonal antibodies of any nonhuman mammalian species could be used in the invention, in practice the antibodies will typically be of rat or murine origin because of the availability of murine and rat cell lines for use in making hybrid cell lines (hybridomas) that produce monoclonal antibodies. These hybridomas are prepared from cells, typically spleen cells that produce antibody to the specified breast cancer antigen and an immortal tumor cell line using the general somatic cell hybridization technique of Kohler, B. and Milstein, C., *Nature* (1975) 256: 495–497.

The antibody-producing fusion partners that are used in the hybridization are generated by immunizing hosts, e.g., mice, with live human breast cancer cells or membrane extracts thereof. The animals are inoculated intraperitoneally with an immunogenic amount of the cells or extract and then boosted with similar amounts of the immunogen. Spleens are collected from the immunized animals a few days after the final boost and a cell suspension is prepared therefrom for use in the fusion. Available murine myeloma lines, such as those from the Salk Institute, Cell Distribution Center, San Diego, Calif., USA, may be used as a tumor fusion partners in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas are expanded, if desired, and supernatants are assayed for anti-human breast cancer activity by conventional immunoassay procedures. The antibodies identified herein as anti-W1 and anti-W9 were prepared, initially selected for selectivity, and characterized using the procedures described in said U.S. patent application Ser. No. 690,750, the disclosure of which as it relates to those antibodies is incorporated herein by reference. These particular antibodies were identified from the group of breast cancer selective antibodies described in said patent application by testing them in an assay that measures inhibition of monoclonal antibody binding to fixed target cells (breast cancer cells) by tumor serum pools relative to normal serum pools. In this manner those antibodies in the group that recognize antigens elevated in serum of breast cancer patients were identified.

Using anti-W1 and anti-W9, the antigen(s) they recognize were purified from serum by affinity chromatography and characterized by sodium dodecyl sulfatepolyacrylamide gel electrophoresis (SDS-PAGE) and Western blottings. The antigen(s) recognized by the antibodies co-purified from serum and exhibited an apparent molecular weight of 260,000 to 340,000 as determined by SDSPAGE. The purification properties of the antigens indicate they may be the same antigen or are closely related or associated molecules.

The amount of W1 and W9 antigen in a serum sample may be determined using available competitive or noncompetitive, direct or indirect assay formats that are available in the art. Radioimmunoassays, enzyme assays, and fluorescent assays are most common. Depending on the particular patient, this determination may be used to detect breast cancer, assess the stage of the disease, or monitor the progress of the disease. Assay formats tested to date have been better at detecting Stage II and above states of cancer than Stage I cancer. When used to detect breast cancer, the amount will be compared to the amount of the antigen that typically occurs in the sera of normal patients. In this regard, the amount in normals will typically be less than about 50 assay units per ml (as determined by the double determinant assay (DDIA) described in the Examples below), whereas in cancer patients, the amount will be in excess of about 50 assay units per ml. When used to assess disease stage the amount will be compared to the amounts that are typical of the various disease states. In this regard, the amounts typical of the stages are: Stage I to III, less than about 100 assay units per ml, and Stage IV, greater than about 100 assay units per ml. When used to monitor the progress of disease, serum samples will be taken periodically (the length of the period will depend upon the patient, and patient history and treatment) from the patient and the amounts of antigen compared with each other. An increase in amount indicates an increase in tumor burden; a decrease indicates decreased tumor burden.

The following examples further describe and illustrate the invention. These examples are not intended to limit the invention in any manner.

EXAMPLES

Monoclonal Antibodies

The panel of antibodies described in U.S. Ser. No. 690,750 was used for evaluation. Antibodies in the panel recognizing antigens on normal liver and spleen were not evaluated, since normal serum levels of antigens present on those organs would be expected to be high. Antibodies were selected for evaluation which recognized antigens present on a high percentage of breast tumors. Thirteen antibodies from the panel were selected for evaluation in an indirect and direct competitive radiometric cell binding assays. These antibodies, their designation in Ser. No. 690,750, isotype, and antigen recognized are listed in Table 1 below. For convenience, the recognized antigens are referred to by the same current designation as are the antibodies. Thus, by way of example, W1 antigen refers to the molecule recognized and bound by monoclonal antibody W1.

TABLE 1

| Designation | | Isotype | Antigen |
|---|---|---|---|
| Current | Previous | | |
| W1 | 2G3 | KG1 | HMW |
| W2 | 9C6 | KM | 75K |
| W3 | 35E10 | KM | 80K |
| W4 | 113F1 | KG3 | 40,60,100,200K |
| W5 | 120H7 | KM | HMW |
| W8 | 219F3 | KG1 | ND |
| W9 | 245E7 | KG1 | HMW |
| W10 | 266B2 | KG1 | 20,55K |
| W11 | 317G5 | KG1 | 42K |
| W12 | 369F10 | KM | HMW |
| W13 | 454C11 | KG2a | 200K |
| W18 | 87H7 | KG1 | 240K |
| W19 | 454A12 | KG1 | 95K |

HMW = high molecular weight; ND = not determined. Molecular weights refer to sizes of antigens identified in breast tumor cell lines.

Cell Binding Assays

Cells

MCF7 cells were obtained from Dr. Marc Lipmann, NIH, and maintained in Dulbecco's Modified Eagle Medium (DMEM) containing 10% fetal calf serum (FCS) and 0.6 μg/ml insulin. Calu-1 cells were obtained from the ATCC and maintained in DMEM containing 10% FCS. For most experiments, cell lines derived from Calu-1 by repeated selection on a FACS were used. These lines bind elevated amounts of W1, W5 and W9 antibodies, and are designated W1S4, W5S4, W9S4, and W5C16. W5C16 was a clonal line derived from W5S4. These derivative cell lines bound more than five fold more $^{125}$I-labeled W1 and W5 antibodies than the parental Calu-1 cells and more than fifty-fold more $^{125}$I-W9 antibody.

Sera

Cells were harvested by trypsinization, seeded at $3-18 \times 10^4$ cells/cm$^2$ in multiwell plastic dishes (48 or 96 well), and maintained at 37° C. for 18 hr prior to initiation of the assay. Monolayers were washed and fixed in situ with 0.5% paraformaldehyde, prior to antibody addition, and block with binding buffer as described by Marquardt, H. and Todaro, G. T., *J Biol Chem* (1982) 257: 5220-5225.

Blood was drawn from individuals and allowed to clot at 23° C. for 10-90 min. Samples were then stored at 4° C.–6° C. for 0.05-5 hr prior to centrifugation $(16,000 \times g)$ in a clinical centrifuge. Serum was separated from the clot, aliquoted and frozen at $-70°$ C.

For the indirect assay pooled serum from 5 normal individuals (NHS) and 5 advanced breast cancer patients (BHS) were used.

For the direct assay sera from a total of 149 individuals were collected. Of these, 34 were diagnosed as having breast cancer. The clinical stage of disease in these individuals at the time of serum collection was designated as follows: Stage I, primary tumor verified, but no involved lymph nodes; Stage II and III, lymph nodes containing tumor cells were present; Stage IV, metastases were present. Sera from eighty-two individuals having types of cancer other than breast were studied; approximately twenty-one of these had colorectal cancers; fifty, prostate cancer; ten, lung cancer; five bladder cancer, four, ovarian cancer; and the rest had cancers of other types. Sera from seven normal volunteers and twenty-six patients hospitalized with nonmalignant diseases were used as controls.

Direct Binding Assay Procedure $^{125}$I-labeled W1, W5, or W9 antibodies (specific activities were approximately $1 \times 10^9$ cpm/-nmole) were added to formalin fixed monolayers of Calu-1 cells at specified concentrations in the presence or absence of competing solutions. The binding reaction was allowed to proceed for 1 hr at 23° C., monolayers were washed with binding buffer, solubilized in 0.5N NaOH, and counted in a gamma counter. Nonspecific antibody binding was measured in the presence of a 50-fold excess of unlabeled antibody and was generally less than 10% of total binding.

Indirect Binding Assay Procedure

Fixed cell monolayers were incubated simultaneously with unlabeled monoclonal antibodies at 0.5 µg/ml in binding buffer and the NHS or BHS sera for a period of 1 hr at 23° C. Monolayers were then washed and incubated with $^{125}$I-labeled goat anti-mouse immunoglobulin (specific activity $1-2 \times 10^9$ cpm/mole) for an additional 1 hr at 23° C. Finally, monolayers were washed twice with binding buffer, solubilized with NaOH and cell-bound radioactivity was determined using a gamma counter.

Results

Indirect Binding Assay

The 13 anti-breast tumor antibodies listed in Table 1 were assayed in three experiments using different serum pools in each experiment. The results are reported in Table 2 below. MCF-7 cells were used in the experiment designated Experiment II. Monoclonal antibodies were added at 0.5 µg/ml in Experiments I and III and at 0.4 µg/ml in Experiments II. $^{125}$I-goat anti-mouse Ig was added at 0.5 µg/ml in Experiment I and at 1 µg/ml in Experiments II and III. Values of antibody bound have been corrected for nonspecific $^{125}$I-antibody binding (antibody bound in the absence of monoclonal antibody). Corrections were 130 pg, 100 pg, and 180 pg for experiments I, II, and III, respectively.

TABLE 2

Inhibition of Antibody Binding by Normal and Tumor Serum Pools

| Antibody | $^{125}$I-Antibody Bound[1] | | % Difference[2] |
|---|---|---|---|
| | NHS | BCS[2] | |
| Experiment I | | | |
| W1 | 2140 | 506 | 76 |
| W2 | 500 | 420 | 16 |
| W3 | 93 | 122 | <1 |
| W4 | 450 | 570 | <1 |
| W5 | 200 | 170 | 15 |
| W8 | 690 | 570 | 17 |
| W9 | 860 | 420 | 51 |
| W10 | 410 | 530 | <1 |
| W12 | 630 | 480 | 24 |
| W13 | 340 | 320 | 6 |
| Experiment II | | | |
| W1 | 550 | 72 | 87 |
| W4 | 212 | 311 | <1 |
| W5 | 91 | 21 | 77 |
| W8 | 190 | 180 | 5 |
| W9 | 180 | 90 | 50 |
| W10 | 400 | 400 | 0 |
| W12 | 130 | 120 | 8 |
| W13 | 150 | 160 | <1 |
| Experiment III | | | |
| W1 | 843 | 170 | 80 |
| W11 | 554 | 520 | 6 |
| W18 | 1380 | 1300 | <1 |
| W19 | 850 | 670 | 21 |

[1]Picograms $^{125}$I-antibody bound per $10^5$ cells.
[2]($^{125}$I bound in NHS-$^{125}$I bound in BCS)/$^{125}$I bound in NHS.

As shown in Table 2, binding of the antibodies W1 and W9 to either cell line was inhibited to a substantially greater extent ($\leq 50\%$) by sea from tumor patients than by sera from normal individuals. The binding of antibody W5 was sometimes substantially inhibited by tumor sera, depending on the particular serum pool used. Binding of all other antibodies tested was not reproducibly inhibited to a significantly greater extent ($\geq 25\%$) by sera from tumor patients.

To determine whether the epitopes recognized by antibodies W1, W5, and W9 were related, the abilities of each antibody to compete for binding of the other antibodies were compared. Each antibody was radiolabeled with $^{125}$I, and fixed concentrations of the labeled antibodies were individually added to target cells in the presence of increasing amounts of unlabeled antibodies. The binding of each radiolabeled antibody was inhibited in a dose dependent fashion by addition of the corresponding unlabeled antibody, an indication that the binding measured was specific. Unlabeled W9 antibody did not inhibit binding of $^{125}$I-W1, even at a fifty-fold excess of unlabeled to labeled antibody. At lower concentrations of unlabeled W9, the binding of W1 was actually slightly, but reproducibly, enhanced. Conversely, unlabeled W1 antibody did not compete for binding of $^{125}$I-W9 at high concentrations, but actually stimulated binding at low concentrations. Since W1 and W9 do not compete with one another for binding, it was concluded that they recognize distinct epitopes.

The behavior of the epitope recognized by W5 is more complex. W5 does not compete for binding of W1 or W9, but in the reciprocal experiment, both W1 and W9 are able to compete for binding of W5. These results suggest that binding of the bulky W5 antibody (IgM isotype) may be inhibited by binding of other antibodies, but that it probably binds to a distinct epitope. This argument is further supported by the finding that W5 antibody binds to a significantly lower proportion of breast tumors tested by immunohistology. In summary, antibodies W1, W5, and W9 appear to recognize distinct epitopes.

Direct Assay

Sera from both normal volunteers and breast cancer patients inhibited in a dose-dependent fashion the binding of $^{125}$I-labeled antibodies W1, W5, and W9 to target cells in this assay. Sera from breast cancer patients generally gave comparable levels of inhibition at significantly higher dilutions than did normal sera. These results confirmed the results of the indirect inhibition assay and indicated that all three antibodies recognize antigen(s) present in elevated levels in serum from breast cancer patients—with the proportion of advanced cancer patients having elevated antigen levels being greater for W1 and W9 than for W5. Both the extent of antigen elevation and the percentage of sera showing elevated antigen levels were lower for W5 than for the other two antibodies indicating that the former was less likely to be useful for serum tests.

To accurately demonstrate the number of patients having elevated W1 and W9 levels, serum samples from a total of 147 individuals were tested for levels of these antigens, using the direct inhibition assay. Of these samples, 34 were from patients with advanced breast cancer, 82 from patients with tumors other than breast, 8 from normal individuals, and 23 from hospitalized patients with nonmalignant disease. To ensure against experimental bias in the determinations, samples were assayed in a random, double-blind fashion. Samples were assayed at a single serum concentration (final serum concentration of 6.25% for W1, 12.5% for W9) and the observed degree of binding inhibition was converted to arbitrary units of the indicated antigen by comparison to an inhibition curve determined for a reference serum. The serum concentrations used for W1 and W9 determinations were chosen such that the median of the observed range of inhibition values approximately coincided with the midpoint of the reference curve; because of this, values at the extreme ends of determined values are less accurate. Values determined are graphically present in FIGS. 1 and 2. A summary of the numbers of individuals with various tumor types having elevated levels of W1 or W9 antigens is presented in Table 3 below.

TABLE 3

| | Summary of Individuals[2] Having Elevated Antigen Levels | | |
|---|---|---|---|
| | Diagnosis | W1 | W9 |
| A. | Malignant Disease | | |
| | Breast (34)[1] | 53 | 74 |
| | Colorectal (21) | 5 | 29 |
| | Prostate (15) | 13 | 33 |
| | Lung (10) | 20 | 50 |
| | Bladder (5) | 40 | 40 |
| | Ovary (4) | 25 | 40 |

TABLE 3-continued

| | Summary of Individuals[2] Having Elevated Antigen Levels | | |
|---|---|---|---|
| | Diagnosis | W1 | W9 |
| | Other (27) | 22 | 15 |
| B. | Nonmalignant Disease | | |
| | Disease (26) | <1 | 12 |
| C. | Normal (7) | <1 | <1 |

[1]Numbers in parentheses indicate the number of individuals tested.
[2]Cut-off values of 50 units/assay and 2 units/assay were used for W1 and W9, respectively.

As shown in FIG. 1, circulating levels of both W1 and W9 antigens were found elevated above normal values in a significant proportion of individuals having breast cancer. In the W1 assay, the highest observed value for a nontumor patient was approximately 50 units: Fifty-three percent (18/34) of individuals with breast cancer and seventeen percent (15/82) of individuals with other malignancies had circulating levels of W1 antigens above this value.

For W9 there was greater overlap between values determined with serum from tumor and normal patients. In this case, most sera from nonmalignant patients and normal controls gave values that clustered around one unit per assay. Twelve percent (4/34) of individuals having nonmalignant diseases had levels of W9 antigen which were significantly elevated from the main cluster of values (>2 units). Seventy-four percent (25/34) of breast tumor patients and approximately twenty nine percent (24/82) of patients with non-breast tumors displayed elevations of serum levels of W9 antigen above the normal cluster. No obvious correlations were noted between serum levels of W1 and W9 antigens and age, sex, estrogen or progesterone receptor levels, or therapeutic regime.

Figure 2:
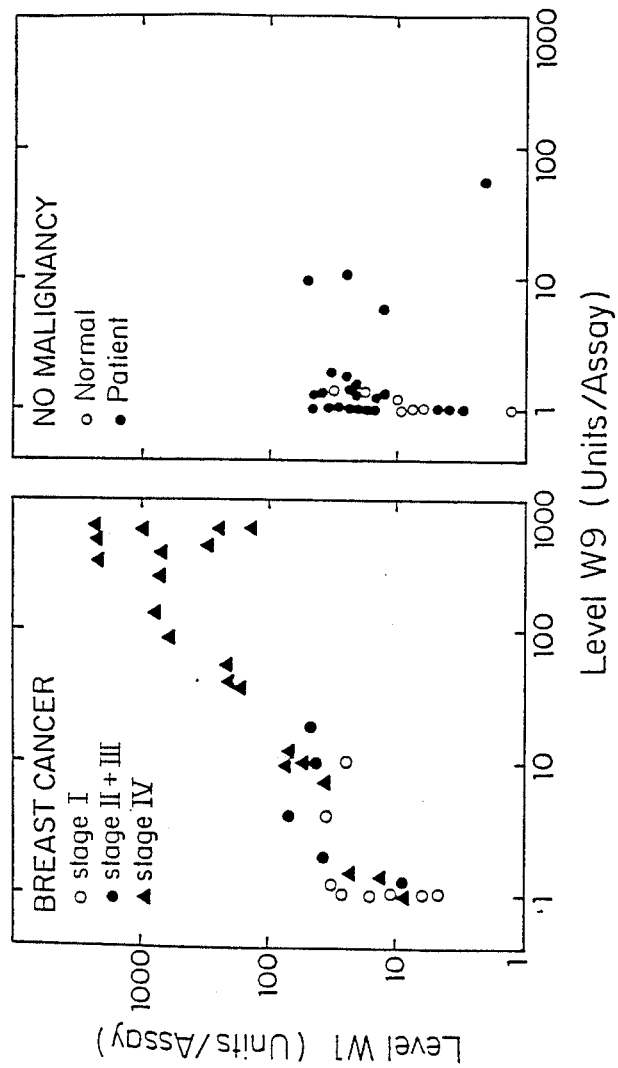

Values determined for serum levels of W1 and W9 antigens from normal individuals and those having breast cancer and nonmalignant diseases are compared in FIG. 2. The data in this figure are also identified according to clinical stages of disease at the time of serum collection. Several points are evident from this depiction of the data. First, values determined for W1 and W9 are generally correlated with each other; a linear relationship exists between W1 and W9 values determined for the same patients. Extreme values tend to correlate less well with each other, but this may well reflect inaccuracies in determining these values. It is also evident that the four noncancer patients having elevated W9 levels did not have correspondingly elevated W1 levels, thereby differentiating them from most breast cancer patients. Finally, levels of both W1 and W9 were generally correlated with clinical stage of disease, with patients having detectable metastases (stage IV) tending to have the highest values of W1 and W9; eighty-six percent (18/21) stage IV patients had W1 and W9 values following clearly outside the normal range (>50 units for W1 and >2 units for W9).

Of patients having tumor types other than breast, some clear differences exist in the numbers of individuals having elevated levels of W1 and W9 antigens (Table 3). In all cases, numbers of the same serum samples positive for W9 were equal to or greater than numbers positive for W1 antigen. These results indicate that elevated levels of W1 and W9 antigens were found in sera from the majority of breast cancer patients. The antigen(s) recognized by these antibodies are characterized in the following section.

Characterization of Antigens

Characterizations of the W1 and W9 antigens present in whole serum was difficult because of the low concentrations of antigen and high amounts of protein present in serum. In order to characterize the antigens recognized by the W1 and W9 antibodies, the W1 antigen was partially purified by immunoaffinity chromatography. Briefly, serum was clarified by centrifugation at 147,000×g for 60 min and mixed with W1 conjugated Sepharose 4B (5 mg antibody/ml resin) at a volume ratio of 4:1 (serum:resin). The mixture was rotated overnight at 4° C., poured into a disposable syringe plugged with glass wool, and washed. Elution of bound antigen was accomplished by addition of 75 mM triethylamine. The column flow-through contained no detectable W1 antigen, while approximately 77% of the initial antigen (as judged by the amount required to inhibit $^{125}$I-W1 binding by 50%) was recovered from the washed column by elution at alkaline pH. The eluate contained approximately 0.57% of the initial protein in the sample, indicating an overall antigen purification of 130-fold. When an immunoaffinity purified preparation of W1 antigen was subjected to SDS-PAGE and Western blotting, two immunoreactive components of approximately Mr=260,000–340,000 daltons were observed.

The same serum sample was assayed for W9 antigen. The W1 affinity column flow-through contained less than 12% of the initial W9 activity, indicating that removal of the W1 antigen also resulted in removal of W9 antigen. W9 activity was eluted from the column with yield of 50%; this corresponds to an overall purification of approximately 88-fold for W9 antigen. When purified W9 antigen was subjected to SDS-PAGE and Western blotting, immunoreactive components were observed which co-migrated with those recognized by W1 antigen. These data indicate that W1 and W9 antigens co-purify from serum and are most likely closely related or associated molecules.

The results shown in FIGS. 1 and 2 were generally confirmed using a double determinant assay (DDIA) with W1 antibody. Sera from 78 breast cancer patients and 75 normal patients were tested. The procedure used in the DDIA was as follows.

Ninety-six (96) well plastic dishes (Immulon II) were coated with a solution of W1 antibody (0.5 μg antibody in a volume of 0.05 ml of 0.05M Tris, pH 8.0) for 1 hr. The plates were then blocked with 1% gelatin in the same buffer for an additional 1 hr. A volume of 0.05 ml of serum (diluted 1:200 in a solution of 5% (w:v), 0.1% (w:v) NaN$_3$ in a 0.05 M Tris, pH 8.0) was added to each test well and the plate was incubated for approximately 16 hr. Wells were then incubated with $^{125}$I-labeled W1 antibody (15 ng in a volume of 0.05 ml), for 30 min, and washed three times with PBS. Bound $^{125}$I-W1 antibody was solubilized with 0.5N NaOH and radioactivity was measured with a gamma counter. Values determined for individual sera were converted to units by comparison with a calibration curve obtained using various dilutions of a reference serum from a breast cancer patient. All incubations were made at 23° C.

Samples of the hybridomas that produce the W1 and W9 monoclonal antibodies described above were deposited in the American Type Culture Collection (ATCC), 12301 Parklawn Drive, Rockville, Md. 20852-1776, U.S.A. The deposit dates and accession numbers for these deposits are listed below.

| Hybridoma/Antibody Designation | | | |
|---|---|---|---|
| Prior | Current | Dep. Date | Accession No. |
| 2G3 | W1 | 27 Jan. 1984 | HB-8491 |
| 245E7 | W9 | 27 Jan. 1984 | HB-8489 |

These deposits were made pursuant to the provisions of the Budapest Treaty and will be maintained in accordance therewith.

Modifications of the invention methods that are obvious to those of skill in technical fields related to the invention are intended to be within the scope of the following claims.

We claim:

1. A method of detecting breast cancer or determining the clinical stage of breast cancer in a human patient comprising:
   (a) providing a sample of body fluid from said human patient; and
   (b) determining the amount of a circulating antigen of about 260–340 kd MW by SDS-PAGE in said body fluid sample by a quantitative immunoassay using a monoclonal antibody to said circulating antigen, wherein said body fluid sample is incubated with said monoclonal antibody to determine the amount of antigen bound by said monoclonal antibody, and said selected antigen being characterized as having an epitope for an antibody produced by hybridoma cell line HB-8491 (W1) or HB-8489 (W9).

2. The method of claim 1 wherein said body fluid is serum.

3. The method of claim 2 wherein said selected antigen is found by the antibody produced by cell line W1.

4. The method of claim 3 wherein said quantitative immunoassay employs as said monoclonal antibody the antibody produced by cell line W1 or an antibody that binds to the same epitope as the antibody produced by cell line W1.

5. The method of claim 3 wherein said quantitative immunoassay employs as said monoclonal antibody the antibody produced by cell line W1.

6. The method of claim 2 wherein said selected antigen is bound by the antibody produced by cell line W9.

7. The method of claim 6 wherein said quantitative immunoassay employs as said monoclonal antibody the antibody produced by cell line W9 or an antibody that binds to the same epitope as the antibody produced by cell line W9.

8. The method of claim 6 wherein said quantitative immunoassay employs as said monoclonal antibody the antibody produced by cell line W9.

9. The method of claim 2 wherein said quantitative immunoassay is a radioimmunoassay employing a radiolabeled antibody selected from the group consisting of said monoclonal antibody and an antibody of said monoclonal antibody.

10. The method of claim 2 wherein said quantitative immunoassay is an enzyme immunoassay employing an enzyme-labeled antibody selected from the group consisting of said monoclonal antibody and an antibody to said monoclonal antibody.

11. The method of claim 2 wherein said quantitative immunoassay is an fluorescent immunoassay employing an fluoroescent antibody selected from the group consisting of said monoclonal antibody and an antibody to said monoclonal antibody.

* * * * *

UNITED STATES PATENT AND TRADEMARK OFFICE
CERTIFICATE OF CORRECTION

PATENT NO. : 4,803,169

DATED : 7 February 1989

INVENTOR(S) : Peter S. Linsley; Vincent W. Ochs; Diane Horn; Joseph P. Brown; all of Seattle, Wash.; David B. Ring, Redwood City, Calif.; Arthur E. Frankel, Chapel Hill, N.C.

It is certified that error appears in the above-identified patent and that said Letters Patent is hereby corrected as shown below:

ON THE COVER PAGE:

On cover page 1, column 1, under the heading "Assignee", please add --Oncogen Limited Partnership, Seattle, Washington--.

Signed and Sealed this

Fourth Day of July, 1989

Attest:

DONALD J. QUIGG

Attesting Officer

Commissioner of Patents and Trademarks